(12) United States Patent
Fisher et al.

(10) Patent No.: US 9,245,169 B2
(45) Date of Patent: Jan. 26, 2016

(54) APPARATUS, SYSTEM, AND METHOD FOR IMAGE NORMALIZATION USING A GAUSSIAN RESIDUAL OF FIT SELECTION CRITERIA

(71) Applicant: Luminex Corporation, Austin, TX (US)

(72) Inventors: Matthew S. Fisher, Austin, TX (US); Nicolas Arab, Austin, TX (US)

(73) Assignee: Luminex Corporation, Austin, TX (US)

( * ) Notice: Subject to any disclaimer, the term of this patent is extended or adjusted under 35 U.S.C. 154(b) by 241 days.

(21) Appl. No.: 13/918,540

(22) Filed: Jun. 14, 2013

(65) Prior Publication Data

US 2013/0336568 A1    Dec. 19, 2013

Related U.S. Application Data

(60) Provisional application No. 61/660,270, filed on Jun. 15, 2012.

(51) Int. Cl.
*G06K 9/00* (2006.01)
*G01N 15/10* (2006.01)
*G01N 15/14* (2006.01)

(52) U.S. Cl.
CPC .......... *G06K 9/0014* (2013.01); *G01N 15/1012* (2013.01); *G01N 15/1456* (2013.01); *G01N 15/1463* (2013.01); *G01N 2015/1006* (2013.01)

(58) Field of Classification Search
None
See application file for complete search history.

(56) References Cited

U.S. PATENT DOCUMENTS

| 3,824,393 | A | 7/1974 | Brain |
|---|---|---|---|
| 6,927,401 | B1 | 8/2005 | Palo |
| 2006/0238757 | A1 | 10/2006 | Silcott |
| 2010/0285594 | A1 | 11/2010 | Purvis, Jr. |
| 2012/0002882 | A1 | 1/2012 | Roth |

OTHER PUBLICATIONS

Ries, Jonas. "Advanced fluorescence correlation techniques to study membrane dynamics." (2008).*
International Search Report and Written Opinion in Application No. PCT/US2013/046035 dated Nov. 29, 2013, 8 pages.

* cited by examiner

*Primary Examiner* — Nirav G Patel
(74) *Attorney, Agent, or Firm* — Meyertons, Hood, Kivlin, Kowert & Goetzel, P.C.

(57) ABSTRACT

An apparatus and method for image normalization using a Gaussian residual of fit selection criteria. The method may include acquiring a two-dimensional image of a plurality of particles, where the plurality of particles comprises a plurality of calibration particles, and identifying a calibration particle by correlating a portion of the image corresponding to the calibration particle to a mathematical model (e.g. Gaussian fit). The measured intensity of the calibration particle may then be used to normalize the intensity of the image.

22 Claims, 3 Drawing Sheets

APPARATUS, SYSTEM, AND METHOD FOR IMAGE NORMALIZATION USING A GAUSSIAN RESIDUAL OF FIT SELECTION CRITERIA

CROSS REFERENCE TO RELATED APPLICATIONS

This application claims the benefit of U.S. Provisional Application No. 61/660,270, filed on Jun. 15, 2012, which is incorporated by reference herein in its entirety.

BACKGROUND OF THE INVENTION

1. Field of the Invention

This invention relates to methods and systems for image data processing and more particularly relates to an apparatus system and method for image normalization using a Gaussian residual of fit selection criteria.

2. Description of the Related Art

Imaging using detectors such as charged coupled device (CCD) detectors is employed in several currently-available instruments in biotechnology applications. Many of the commercially available systems are configured to image target human (or other animal) cells. For multiplexed applications in which CCD detectors are used to measure fluorescent emission of cells, the position of the cells and the fluorescent emission within the image may be used to characterize the cells.

SUMMARY OF THE INVENTION

An method for normalizing an image is presented. In one embodiment, the method includes acquiring a two-dimensional image of a plurality of particles, where the plurality of particles comprises a plurality of calibration particles. In addition, the method may include the step of identifying a calibration particle by correlating a portion of the image corresponding to the calibration particle to a mathematical model. Furthermore, the method may include measuring an intensity of the calibration particle and utilizing the intensity of the calibration particle to normalize the intensity of the image.

In some embodiments, the calibration particle is internally dyed. In some embodiments, the method may also include identifying a plurality of calibration particles, where the plurality of calibration particles are distributed into a plurality of regions of the two-dimensional image. In addition, the method may include utilizing an intensity of the plurality of calibration particles to normalize an intensity of the plurality of regions.

In some embodiments, the method may include utilizing the intensity of the calibration particle to normalize the intensity of a second two-dimensional image of the plurality of particles. For example, the second two-dimensional image may be a classification image.

In some embodiments, the mathematical model may be a Gaussian mathematical model. In some embodiments, the mathematical model may be a quadratic mathematical model.

In some embodiments, measuring the intensity of the calibration particle may include detecting a peak of the calibration particle. In addition, measuring the intensity of the calibration particle may include integrating an area of the image around a center of the calibration particle.

In some embodiments, the method may include subtracting a background signal from the two-dimensional image before identifying the calibration particle.

Tangible computer-readable media are also presented. The tangible computer-readable media may include instructions, that when executed by a computer, cause the computer to perform the methods described herein.

The term "coupled" is defined as connected, although not necessarily directly, and not necessarily mechanically.

The terms "a" and "an" are defined as one or more unless this disclosure explicitly requires otherwise.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
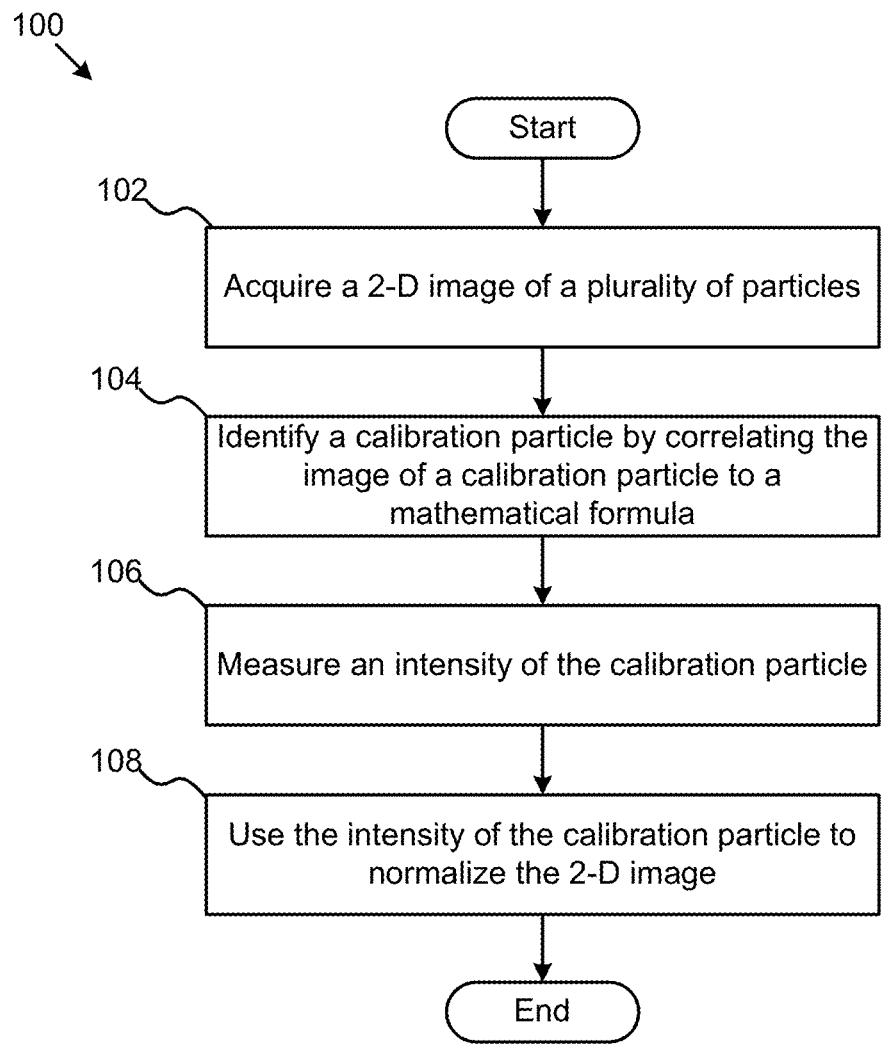
FIG. 1 is a flow chart illustrating one embodiment of a method for normalizing an image.

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, or non-organic matter, for example. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. Without limitation, the systems and methods described herein may be used with any of the particles described in these patents. In addition, particles for use in method and system embodiments described herein may be obtained from manufacturers such as Luminex Corporation of Austin, Tex.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated and described in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein also include particles having one or more fluorochromes or fluorescent dyes incorporated into the core of the particles. For example, calibration particles may be internally and uniformly dyed. In some embodiments a calibration particle may be internally dyed with a plurality of dyes.

Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles. As described below, image data processing may include classification of the particles, particularly for a multi-analyte fluid, as well as a determination of the amount of analyte bound to the particles. Since a reporter signal, which represents the amount of analyte bound to the particle, is typically unknown during operations, specially dyed particles, which not only emit fluorescence in the classification wavelength(s) or wavelength band(s) but also in the reporter wavelength or wavelength band, may be used for the processes described herein.

The methods described herein generally include analyzing one or more images of particles and processing data measured from the images to determine one or more characteristics of the particles. For example, the processing of data may be used to determine normalized numerical values representing the magnitude of fluorescence emission of the particles at multiple detection wavelengths in multiple regions of an image. Subsequent processing of the one or more characteristics of the particles, such as using one or more of the numerical values to determine a token ID representing the multiplex subset to which the particles belong and/or a reporter value representing a presence and/or a quantity of analyte bound to the surface of the particles, can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al., which are incorporated by reference as if fully set forth herein.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

FIG. 1 illustrates one embodiment of a method 100 for image normalization using a mathematical model (e.g. Gaussian) residual of fit selection criteria. In one embodiment, the method 100 begins with the step 102 of acquiring a two-dimensional image of a plurality of particles. The image may be taken, for example, with a CCD sensor. In some embodiments, multiple images may be taken. For example, two classification channel images and a reporter image may be taken. The plurality of particles may include a plurality of calibration particles. Calibration particles may be, for example, triple-dyed particles. The dyes may be evenly distributed throughout the calibration particles, which may result in an evenly distributed fluorescence in the reporter channel when the calibration particles are illuminated with an excitation light source. In some embodiments, all particles (calibration particles and assay particles) will have evenly distributed fluorescence in the classification channels. However, only calibration particles will have evenly distributed fluorescence in the reporter channel. Evenly distributed fluorescence may cause a Gaussian distribution of light in an image corresponding to the particle due to the spherical shape of a particle.

Step 104 recites identifying a calibration particle by correlating a portion of the image that corresponds to the calibration particle to a mathematical formula. This step may include some sub-components. For example, the method may first include subtracting out a background signal from the image and then detecting the peaks in the image that correspond to individual particles. Once the location of the particles are known, the method may include performing a numerical fit to the image pixels around the detected peaks. In one embodiment, the numerical fit may be a Gaussian fit of the equation in the form of:

$$G(u,v)=a^{*}e^{-b^{*}(u^{2}+v^{2})}$$

The fit process determines the parameters a and b that best fit the image of the particle. The fit may be done in sub-pixel resolution, such as by interpolating pixels to increase the resolution of the image used to perform the fit. The residual of the fit may be measured and if the residual is above a predetermined value (a tolerance), the particle may be rejected as not being a calibration particle. Calibration particles may have Gaussian profiles due to being internally dyed. By contrast, assay particles, which may have fluorescence solely on the surface of the particle, may not have a Gaussian distribution. As such, calibration particles may be identified by their Gaussian profiles. Although the profiles of calibration particles is described generally as Gaussian, in some embodiments, the mathematical formula to perform the fit may be quadratic, for example. Different formulas may reduce the processing required to determine the fit at the expense of reduced accuracy in detecting calibration particles. In addition, in practice, additional steps, such as discarding outlier particles, may be used to increase the performance of the system.

Method 100 also includes the step 106 of measuring an intensity of the calibration particle. The intensity of the particle may be measured by measuring the peak of the measured signal, or it may be measured by integrating the pixels within a particular radius of the measured peak. Additionally, the intensity may be measured by first determining a sub-pixel image of the particle, such as through interpolation, and then integrating the sub-pixel image around a peak of the particle.

Certain parameters of that calibration particle are known. For example, a calibration particle may have a known size and amount of fluorescent material that are established when the calibration particles are manufactured. For example, the amount of different dyes used to manufacture the calibration particles can be carefully controlled to ensure a known amount and even distribution of fluorescence.

Method 100 also includes the step 108 of using the intensity of the calibration particle to normalize the two-dimensional image. Because the expected amount of fluorescence of the calibration particle is known, that amount of fluorescence may be used to normalize the measured amount of fluorescence intensity. Moreover, this process may be repeated for a plurality of calibration particles distributed throughout the 2-D image to normalize different areas of the image. Because calibration particles can be interspersed with assay particles, the image may be normalized without having to take a separate image with calibration particles alone. Thus, the throughput may be increased while maintaining normalized intensity of multiple images. The lack of uniformity of image intensity may be caused by light source non-uniformity, lens nonuniformity, or movement of the imaging plane, for example. The methods described herein may be able to simultaneously normalize for a plurality of causes of non-uniform light measurements.

The normalization of the image intensity may be used when multiple images are taken of the same set of particles. For example, two separate images may be taken of classification channel and one in a reporter channel. The calibration particles may show up in all three images and may be used to normalize all three images.

Figure 2:
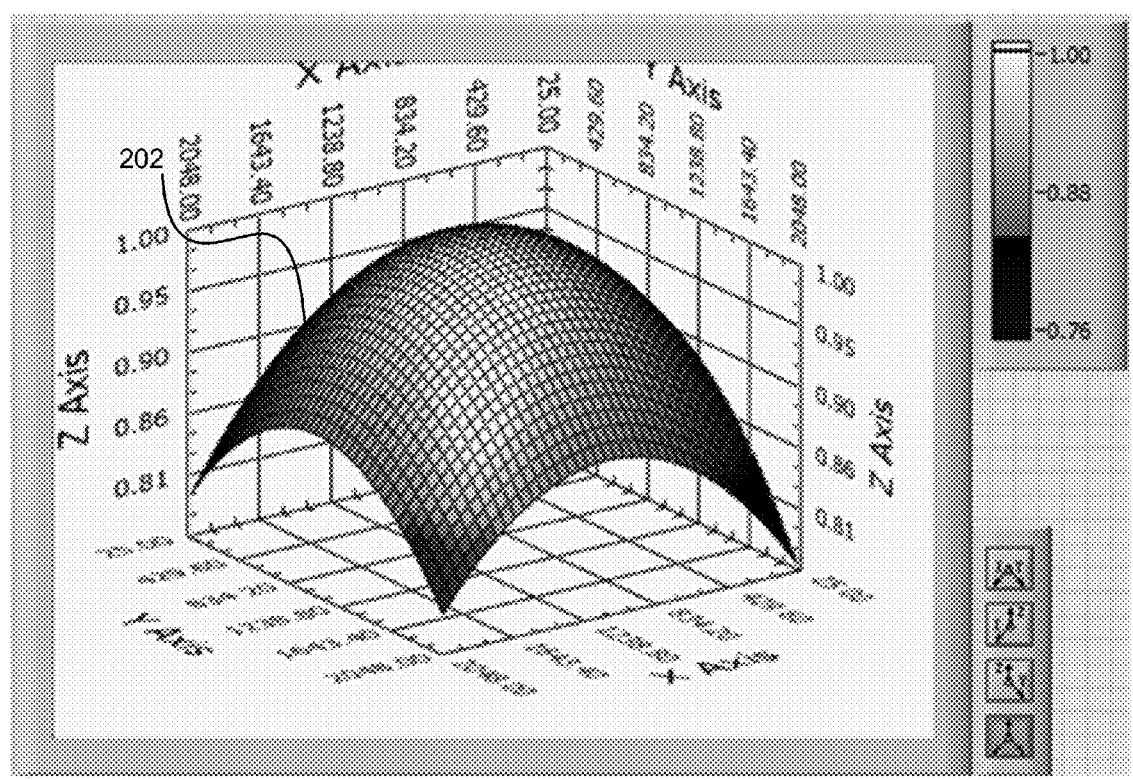
FIG. 2 is a three-dimensional representation of a two-dimensional image of a calibration particle.

FIG. 2 describes a portion of a two-dimensional image where the intensity of measured light 202 from a particle is shown on the z-axis. In this situation, the measured light 202 is Gaussian in form. That information may be used to identify a particle as a calibration particle as described above.

Figure 3:
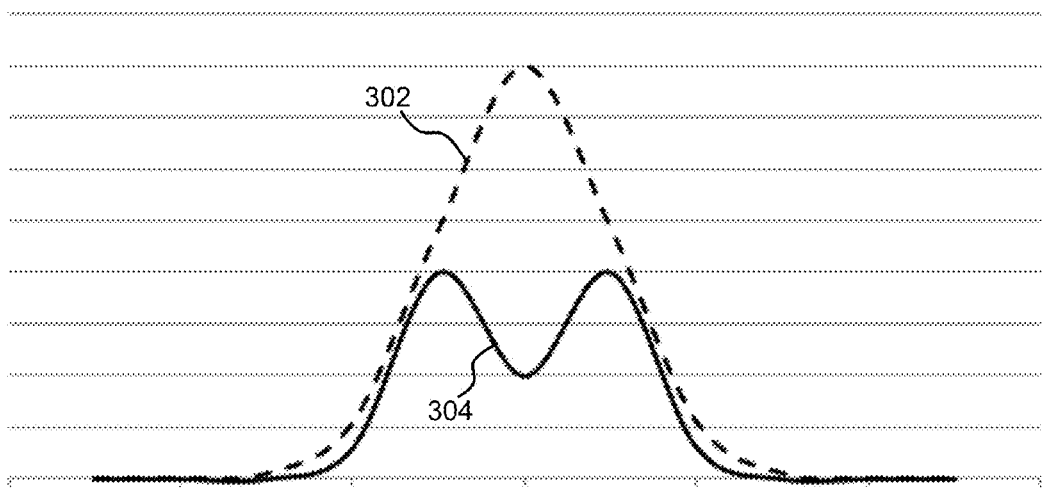
FIG. 3 is a cross-sectional view of images of two particles.

FIG. 3 shows example profiles of two different particles. Curve 302 corresponds to a Gaussian curve. By fitting the curve to a Gaussian fit, the particle whose image corresponds to curve 302 may be identified as a calibration particle. By contrast, curve 304 may correspond to a an assay particle (non-calibration particle). In this example, the detected fluorescence may come from material distributed on the surface of the particle. As such, the distribution of light will not be Gaussian and the particle can be identified as not being a calibration particle. These curves correspond to a cross section of the image shown in FIG. 2.

Figure 4:
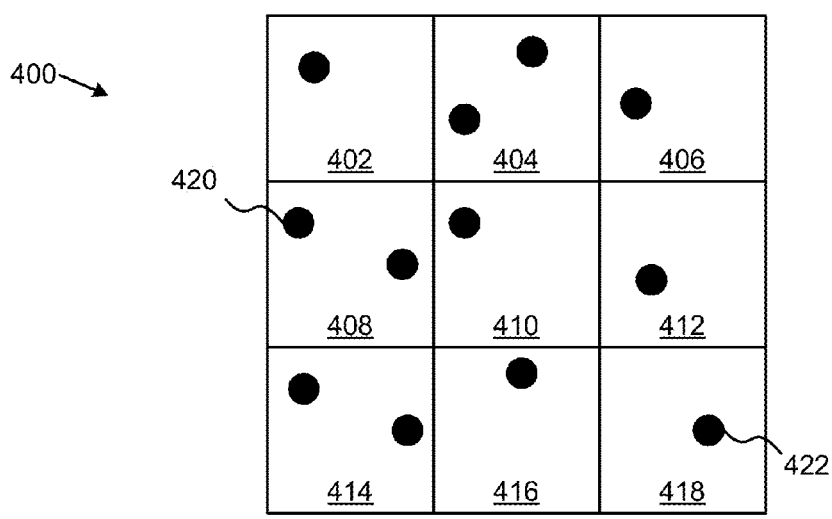
FIG. 4 is a representation of a two-dimensional image partitioned into nine regions for normalization.

FIG. 4 shows one example of how calibration particles 420 may be used to normalize an image. In this example, the image 400 is partitioned into nine regions (402, 404, 406, 408, 410, 412, 414, 416, and 418). Each region has one or more calibration particles 420. As described above, according to methods described herein, the calibration particles may be first identified as being calibration particles by the profile of their image. After the calibration particles are identified, the intensity of the calibration particles 420 may be measured as described above. That measured intensity may then be used to normalize measurements of non-calibration particles (not shown) in the image 400. Differences in image intensity, such as may be introduced by lighting non-uniformities, lens aberrations, or sensor imperfections, for example, may be compensated through this normalization. Although the example in FIG. 4 shows an image that is partitioned into nine regions, the partitions may be as few as one (the entire image is normalized uniformly, or may be unlimited. In the latter situation, a mathematical formula representing the normalization may be constructed. For reasons of explanation only, the mathematical formula representing the normalization may resemble a topographical map that shows how amount of normalization applies varies by location on the image.

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated and described in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation of Austin, Tex. The terms "particles" and "microspheres" are used interchangeably herein.

Some embodiments include a tangible computer-readable medium that includes computer-readable code that, when executed by a computer, causes a computer to perform at least one embodiment of the present methods. The tangible computer-readable medium may be, for example, a CD-ROM, a DVD-ROM, a flash drive, a hard drive or any other physical storage device.

In some methods, a tangible computer-readable medium is created. In some embodiments, the method may include recording the computer readable medium with computer readable code that, when executed by a computer, causes the computer to perform at least one embodiment of the present methods. Recording the computer readable medium may include, for example, burning data onto a CD-ROM or a DVD-ROM, or otherwise populating a physical storage device with the data.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. For example, the fits used to identify calibration particles are described as preferably being Gaussian fits. Other mathematical fits may be used that are within the spirit of the disclosed embodiments. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A method comprising:
    acquiring a two-dimensional image of a plurality of particles, wherein the plurality of particles includes a plurality of calibration particles having Gaussian intensity profiles based on internal distributions of a first fluorescent material, and a plurality of non-calibration particles having non-Gaussian intensity profiles based on surface distributions of a second fluorescent material;
    identifying a calibration particle of the plurality of calibration particles by correlating a portion of the image corresponding to the calibration particle to a Gaussian function;
    measuring an intensity of the calibration particle; and
    normalizing an intensity of the image based at least in part on the intensity of the calibration particle.

2. The method of claim 1, wherein the two-dimensional image is an image in a reporter channel.

3. The method of claim 1, further comprising:
    identifying a plurality of calibration particles, wherein the plurality of calibration particles are distributed into a plurality of regions of the two-dimensional image; and
    normalizing an intensity of the plurality of regions based at least in part on an intensity of the plurality of calibration particles.

4. The method of claim 1, further comprising normalizing an intensity of a second two-dimensional image of the plurality of particles based at least in part on the intensity of the calibration particle.

5. The method of claim 4, wherein the second two-dimensional image is a classification image.

6. The method of claim 1, wherein measuring the intensity of the calibration particle includes detecting a peak of the calibration particle.

7. The method of claim 1, wherein measuring the intensity of the calibration particle includes integrating an area of the image around a center of the calibration particle.

8. The method of claim 1, further comprising subtracting a background signal from the two-dimensional image before identifying the calibration particle.

9. A non-transitory, computer-readable medium comprising machine-readable instructions for:
    acquiring a two-dimensional image of a plurality of particles, wherein the plurality of particles includes a plurality of calibration particles having Gaussian intensity profiles based on internal distributions of a first fluorescent material, and a plurality of non-calibration particles having non-Gaussian intensity profiles based on external distributions of a second fluorescent material;
    identifying a calibration particle of the plurality of calibration particles by correlating a portion of the image corresponding to the calibration particle to a Gaussian function;
    measuring an intensity of the calibration particle; and
    adjusting a brightness of the image based at least in part on the intensity of the calibration particle.

10. The non-transitory, computer-readable medium of claim 9, wherein the two-dimensional image is an image in a reporter channel.

11. The non-transitory, computer-readable medium of claim 9, wherein the instructions are further for:
    identifying a plurality of calibration particles, wherein the plurality of calibration particles are distributed into a plurality of regions of the two-dimensional image; and
    adjusting brightnesses of the plurality of regions based at least in part on intensities of the plurality of calibration particles.

12. The non-transitory, computer-readable medium of claim 9, further comprising adjusting a brightness of a second two-dimensional image of the plurality of particles based at least in part on the intensity of the calibration particle.

13. The non-transitory, computer-readable medium of claim 12, where the second two-dimensional image is a classification image.

14. The non-transitory, computer-readable medium of claim 9, wherein measuring the intensity of the calibration particle includes detecting a peak of the calibration particle.

15. The non-transitory, computer-readable medium of claim 9, wherein measuring the intensity of the calibration particle includes integrating an area of the image around a center of the calibration particle.

16. The non-transitory, computer-readable medium of claim 9, wherein the instructions are further for subtracting a background signal from the two-dimensional image before identifying the calibration particle.

17. An apparatus, comprising:
    at least one processor; and
    an imaging subsystem;
    wherein the imaging subsystem is configured to:
        accept, into an imaging region of the apparatus, a plurality of particles that includes calibration particles having Gaussian intensity profiles based on internal distributions of a first fluorescent material, and reporter particles having non-Gaussian intensity profiles based on non-internal distributions of a second fluorescent material;
        supply light to the imaging region; and
        capture an image of the plurality of particles; and
    wherein the at least one processor is configured to:
        identify at least one of the calibration particles by correlating a portion of the image corresponding to the calibration particle to a Gaussian function;
        measure an intensity of the calibration particle; and
        normalize an intensity of the image based at least in part on the intensity of the calibration particle.

18. The apparatus of claim 17, wherein the correlating the portion of the image corresponding to the calibration particle to the Gaussian function includes approximating the Gaussian function with a quadratic function.

19. The apparatus of claim 17, wherein the imaging subsystem includes a CCD detector.

20. The apparatus of claim 17, wherein the at least one processor is further configured to:
    identify a plurality of calibration particles;
    measure intensities of the plurality of calibration particles; and
    normalize intensities of a corresponding plurality of regions of the image based at least in part on the intensities of the plurality of calibration particles.

21. The apparatus of claim 20, wherein the plurality of regions is based on a grid that partitions the image into the regions.

22. The apparatus of claim 20, wherein the plurality of regions is a continuous plurality of regions.

* * * * *